(12) United States Patent
Sahin et al.

(10) Patent No.: US 11,603,827 B1
(45) Date of Patent: Mar. 14, 2023

(54) SYSTEMS AND METHODS FOR FABRICATING WATER-RESPONSIVE ACTUATORS

(71) Applicant: THE TRUSTEES OF COLUMBIA UNIVERSITY IN THE CITY OF NEW YORK, New York, NY (US)

(72) Inventors: Ozgur Sahin, New York, NY (US); Onur Cakmak, New York, NY (US); Xi Chen, New York, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 663 days.

(21) Appl. No.: 16/408,659

(22) Filed: May 10, 2019

Related U.S. Application Data

(63) Continuation-in-part of application No. PCT/US2017/061368, filed on Nov. 13, 2017.
(Continued)

(51) Int. Cl.
*F03G 7/06* (2006.01)
*C12N 1/12* (2006.01)
(Continued)

(52) U.S. Cl.
CPC ............... *F03G 7/06* (2013.01); *B05D 3/067* (2013.01); *B05D 7/24* (2013.01); *B29C 65/4845* (2013.01);
(Continued)

(58) Field of Classification Search
CPC .......... F03G 7/06–067; B29C 65/4845; B05D 3/067; B05D 7/24; B05D 2401/20
See application file for complete search history.

(56) References Cited

U.S. PATENT DOCUMENTS 3,016,691 A * 1/1962 Asakawa .................. F03G 7/06
33/DIG. 19
6,747,259 B1 * 6/2004 Quinn .................... H05K 3/305
257/E27.13
(Continued)

FOREIGN PATENT DOCUMENTS

CN 102285183 A * 12/2011
CN 102285183 A   12/2011
(Continued)

OTHER PUBLICATIONS

Chen, X., Goodnight, D., Gao, Z. et al. Scaling up nanoscale water-driven energy conversion into evaporation-driven engines and generators. Nat Commun 6, 7346 (2015). https://doi.org/10.1038/ncomms8346 (Year: 2015).*
(Continued)

*Primary Examiner* — Mark A Laurenzi
*Assistant Examiner* — Xiaoting Hu
(74) *Attorney, Agent, or Firm* — Baker Botts L.L.P.

(57) ABSTRACT

Water-responsive actuators and methods for creating water responsive actuators are disclosed. In some embodiments, the disclosed subject matter includes a first layer, for example a plastic tape, and a second layer, for example bacterial spores and cured adhesive. The second layer can be created in a pattern. The pattern can include joints, which can contract when exposed to dry air and can thereby bend the actuator, and can expand when exposed to humid air and thereby return the actuator its original position.

10 Claims, 6 Drawing Sheets

Related U.S. Application Data

(60) Provisional application No. 62/421,014, filed on Nov. 11, 2016.

(51) Int. Cl.
*C12N 1/20* (2006.01)
*B05D 7/24* (2006.01)
*B29C 65/48* (2006.01)
*C12N 1/02* (2006.01)
*B05D 3/06* (2006.01)
*C12R 1/07* (2006.01)
*C12R 1/125* (2006.01)

(52) U.S. Cl.
CPC ............... *C12N 1/02* (2013.01); *C12N 1/125* (2021.05); *C12N 1/205* (2021.05); *B05D 2401/20* (2013.01); *C12R 2001/075* (2021.05); *C12R 2001/125* (2021.05)

(56) References Cited

U.S. PATENT DOCUMENTS

| | | | |
|---|---|---|---|
| 7,381,583 B1 | 6/2008 | Ebel et al. | |
| 9,234,508 B2 | 1/2016 | Sahin | |
| 2006/0269998 A1 | 11/2006 | Buck et al. | |
| 2013/0285386 A1* | 10/2013 | Sahin | H02N 2/18 60/516 |
| 2014/0030487 A1 | 1/2014 | Boyce et al. | |
| 2016/0033389 A1 | 2/2016 | Serpe | |
| 2016/0054248 A1 | 2/2016 | Martin et al. | |
| 2016/0121546 A1* | 5/2016 | Yao | B29C 64/364 428/221 |
| 2016/0278384 A1 | 9/2016 | Jabs et al. | |

FOREIGN PATENT DOCUMENTS

| | | |
|---|---|---|
| WO | WO 97/08458 A1 | 3/1997 |
| WO | WO 2015/172067 A1 | 11/2015 |
| WO | WO 2017/010945 A1 | 1/2017 |

OTHER PUBLICATIONS

International Search Report dated Feb. 2, 2018 in International Application No. PCT/US17/61368.
Chen et al., "Bacillus Spores as Building Blocks for Stimuli-Responsive Materials and Nanogenerators," Nature Nanotechnology 9(2):137-141 (2014).
Chen et al., "Scaling up nanoscale water-driven energy conversion into evaporation-driven engines and generators," Nature Communications 6:7346-7353 (2015).
Dai et al., "Humidity-Responsive Bilayer Actuators Based on a Liquid-Crystalline Polymer Network," Appl. Mater. Interfaces 5:4945-4950 (2013).
Ou et al., "bioPrint: an Automatic Deposition System for Bacteria Spore Actuators," UIST' 14 Adjunct Proceedings, Oct. 2014 (3 pages).
Shoji et al., "Temperature, humidity, and dimension dependence of the bending motion of ionomer-based polymer actuators," Polymers for Adv. Tech. 27:1458-1464 (2016).
Zhang et al., "Directed Motility of Hygroresponsive Biomimetic Actuators," Adv. Functional Materials 26:1040-1053 (2016).
PI: Najfi K, Awardee Organization: University of Michigan Ann Arbor, Force through transpiration: biomimetic nanomechanical actuation, 2006, NSF Grant #: 0556271 [Accessed on Jan. 15, 2020].

* cited by examiner

SYSTEMS AND METHODS FOR FABRICATING WATER-RESPONSIVE ACTUATORS

CROSS REFERENCE TO RELATED APPLICATION

This application is a continuation-in-part of International Patent Application No. PCT/US17/061368, filed Nov. 13, 2017, which claims the benefit of priority of U.S. Provisional Patent Application No. 62/421,014 filed Nov. 11, 2016, which is hereby incorporated by reference in its entirety.

STATEMENT REGARDING FEDERALLY SPONSORED RESEARCH

This invention was made with government support under N00014-16-1-2449 awarded by Navy/ONR. The government has certain rights in the invention.

BACKGROUND

Humidity responsive actuators can be a versatile technology for various applications from power generation to soft robotics. Actuation can be maintained by fluctuating ambient humidity externally or within the limits of natural fluctuations.

Materials such as graphene oxide, polymers, liquid crystals, paper, and biologically based materials can be used to create humidity responsive actuators. Certain polymer based actuators can exhibit limited work density due to their low Young's Modulus. Graphene oxide, in contrast, can enable stiffer devices but can present challenges when attempting to pattern complicated geometries in a scalable way. Printing based techniques can be used to achieve programmable humidity responsive actuators, but such actuators can require long process times to fabricate complicated geometries.

The spatial gradients of relative humidity near evaporating surfaces can provide a source for humidity responsive actuators, especially for power generation applications. However, certain actuators exhibit limited resistance to direct liquid water contact. For example, certain polymer based and paper based actuators can be prone to taking up excessive amount of water when soaked inside water, resulting in an irreversible expansion in their size. Their function, shapes and characteristics can be substantially affected by the water uptake and subsequent drying. This can make them prone to failure when operated very close to water surfaces, which bars their usage nearby the aqueous environments.

Additionally, preserving functionality after liquid water contact can be a challenge for certain humidity responsive materials, for example polymer based and paper based actuators. Some humidity responsive actuators' function, shape and characteristics change after such liquid water contact. Actuators that have limited functionality retention after liquid water contact can be of limited suitability for applications in which they come into contact with liquids, for example, in biological applications near skin, in marine applications near water including; in the generation of stroke, in outdoor conditions in weather, in the interface between different liquids such as oils, solvents, or water, among others.

Accordingly, there exists a need for a technique for efficiently creating water-responsive actuators that can respond to humidity or liquid water and can have improved functionality retention after liquid water contact.

SUMMARY

Systems and methods for fabricating water-responsive actuators are disclosed herein.

In some embodiments, methods for fabricating a water-responsive actuator using a solution including bacterial spores and a UV-curable adhesive suspended in a solvent are disclosed. An example method includes depositing the solution onto a substantially planar layer of flexible material that substantially maintains its shape in the presence of water, applying UV light to the deposited solution to cure at least a portion of the deposited solution to form a water-responsive layer, and removing deposited solution which remains uncured.

In some embodiments, the bacterial spores are *Bacillus subtilis* or *Bacillus thuringiensis*. The bacterial spores and the UV-curable adhesive can be provided in a ratio of about 1:1 by volume, about 13:7 by volume, about 3:2 by volume or other suitable ratios. The UV-curable adhesive can have a Young's Modulus of about 1-2 GPa. In some embodiments, the UV-curable adhesive can have a Young's Modulus of about 0.5-2 GPa.

The disclosed subject matter also provides water-responsive actuators. In some embodiments, an actuator includes a substantially planar first layer of a flexible material that substantially maintains its shape in the presence of water, and a second layer positioned on a surface of the first layer. The second layer can include a cured solution including a bacterial spore and a cured adhesive, and be water-responsive to permit repeatable actuation in the presence of water.

The second layer can be a patterned layer. The actuator can include an electrical heater adapted to affect local humidity. The second layer can be adapted to be electrically conductive. The second layer can be adapted for actuation by contact with liquid water, or by contact with air, e.g., having a relative humidity of at least 30%. In some embodiments, the second layer can be adapted for actuation by contact with air having a first relative humidity and to return to an initial shape by contact with air having a second relative humidity, e.g., the second relative humidity being at least 10% less than said first relative humidity.

The disclosed subject matter also provides solutions for making a water-responsive material. In some embodiments, the solution includes a UV curable adhesive, a water-responsive bacterial spore, and a solvent. The adhesive can be provided in a ratio of about 25% to about 50% by volume to the solution. In some embodiments, the adhesive can be provided in a ratio of about 0.1% to about 5% by volume to the solution. The adhesive can be cured by light having a wavelength between about 200 nanometers and about 700 nanometers.

The accompanying drawings, which are incorporated and constitute part of this disclosure, illustrate embodiments of, and serve to explain the principles of, the disclosed subject matter.

Figure 1:
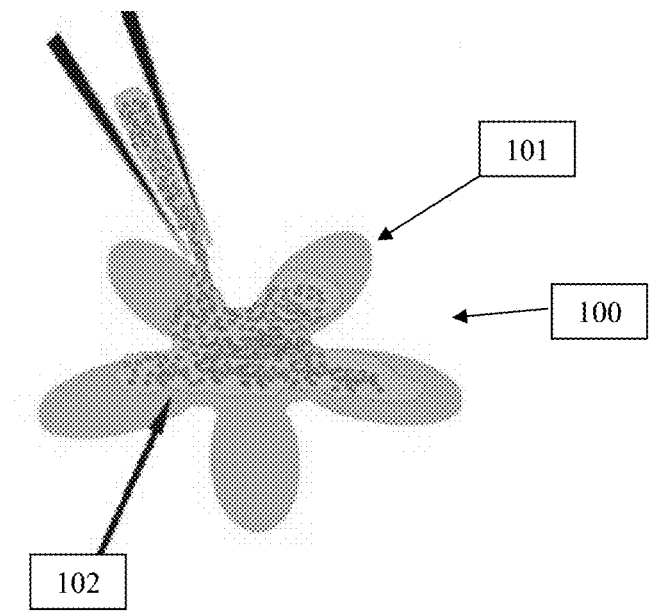
FIG. 1 is an illustration of a method for fabricating a water-based actuator in accordance with some embodiments of the disclosed subject matter.

Throughout the drawings, the same reference numerals and characters, unless otherwise stated, are used to denote like features, elements, components or portions of the illustrated embodiments. Moreover, while the disclosed subject matter will now be described in detail with reference to the Figs., it is done so in connection with the illustrative embodiments.

DETAILED DESCRIPTION

Techniques for making water-responsive actuators, solutions for such actuators, and water-responsive actuators are presented. Environmental free energy from evaporation and humidity gradients is significant, and water-responsive actuators can make use of this energy. Water-responsive materials deposited on substrates can cause those substrates to move in response to water or changes in relative humidity, making a water-responsive actuator. Bacterial spores are a water-responsive biological material that can demonstrate a high energy density, high reversibility, and relatively fast response to variations in water potential. Bacterial spores can be dormant and change shape during hydration and dehydration, which can be used to generate mechanical work. They can also be deposited onto substrates with adhesives that cure in the presence of UV light, and in patterns by exposing only some areas to UV light. The patterns can affect how the substrate moves when exposed to water.

Referring to FIG. 1, an illustration of an example method for fabricating a water-based actuator is shown. An example actuator 100 can include a substantially planer first layer 101 of flexible material that substantially maintains its shape in the presence of water, either in liquid form or in the form of humidity, for example, a plastic tape. For example, material that changes shape up to 10% can be suitable for this layer. An uncured solution 101, can be deposited onto the first layer 101. In certain embodiments, the flexible material can include fleece, cotton, polyester, nylon, spandex, wool, and/or combinations thereof. In non-limiting embodiments, the flexible material can be a moisture permeable material.

This first layer 101 can be polyimide film, for example Kapton Tape (Colepalmer). This first layer 101 can be cellulose based film, for example Cellophane film, mylar, or a silicone based elastomer. The first layer 101 can be cut into shapes by, for example, a laser cutter such as the Epilog Mini 24, $CO_2$ laser system. In some embodiments, the solution 102 can be deposited using spray coating, spin coating, printing, dipping or as seen in FIG. 1, manual pipetting.

Figure 2:
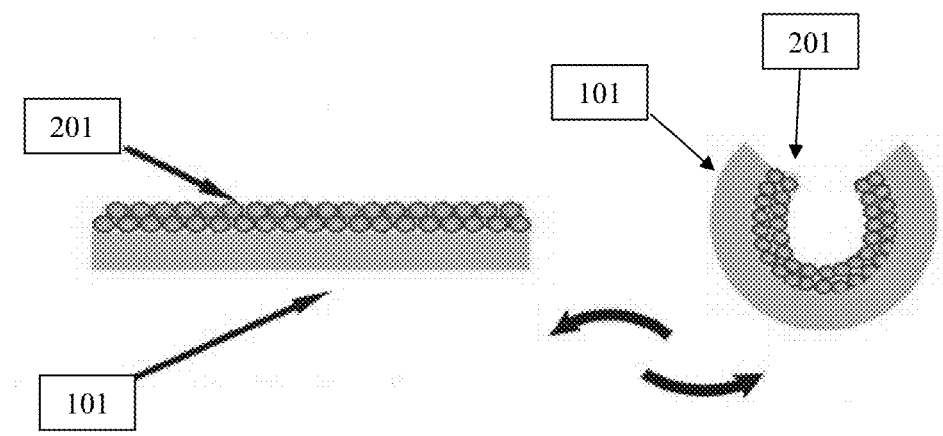
FIG. 2 is an illustration of a water-based actuator in accordance with some embodiments of the disclosed subject matter.
Figure 3:
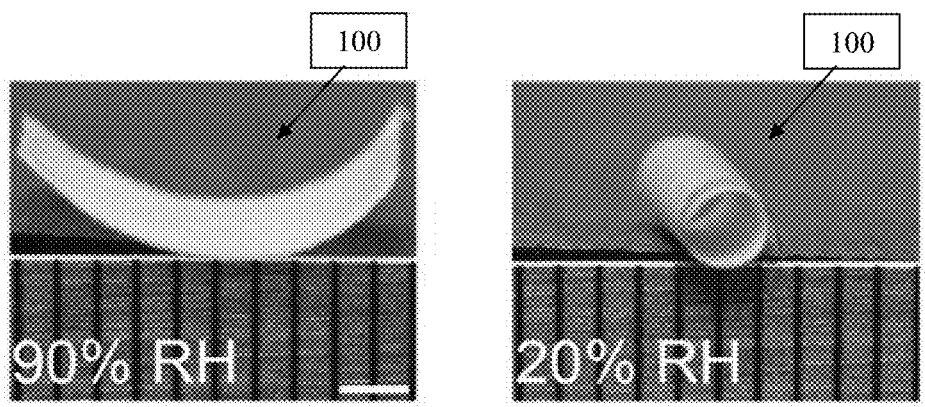
FIG. 3 is an image of an example water-based actuator in accordance with some embodiments of the disclosed subject matter.

Referring to FIGS. 2 and 3, an example actuator 100 is shown. An actuator 100 can include a first layer 101 as described in connection with FIG. 1, and a second layer 102. The second layer 102 can be a water-responsive layer. The second layer 102 can contract when exposed to dry air, for example 20% relative humidity, and can thereby bend the first layer 100 as seen in FIGS. 2 and 3. The second layer 102 can expand when exposed to humid air, for example, 90% relative humidity, and can thereby return the first layer 100 to its original position, as seen in FIGS. 2 and 3. In some embodiments, the second layer 102 can be patterned. The patterning can define active and passive parts.

In some embodiments, a conductive adhesive or ink can be added to the solution 102 and actuation can be maintained through resistive heating of the second layer 201. This adhesive can be UV-curable and can include, for example, silver. In other embodiments, a conductive polymer can be mixed with the solution 102 to maintain resistive heating in the second layer 201. This conductive polymer can be, for example, PEDOT:PSS (Poly(3,4-ethylenedioxythiophene)-poly (styrenesulfonate)), and can have conductivity values between about $1*10^{-5}$ S/cm and about $1*10^5$ S/cm. A light source (not shown) can be utilized to affect local humidity. This light can be, for example, a laser or LED and can be part of the actuator. The wavelength of this light can be between about 300 nanometers and about 4 micrometers, in visible wavelengths or infrared wavelengths.

The term "about" or "approximately" means within an acceptable error range for the particular value as determined by one of ordinary skill in the art, which will depend in part on how the value is measured or determined, i.e., the limitations of the measurement system. For example, "about" can mean within three or more than three standard deviations, per the practice in the art. Alternatively, "about" can mean a range of up to 20%, preferably up to 10%, more preferably up to 5%, and more preferably still up to 1% of a given value. Also, particularly with respect to systems or processes, the term can mean within an order of magnitude, preferably within five-fold, and more preferably within two-fold, of a value.

Figure 4:
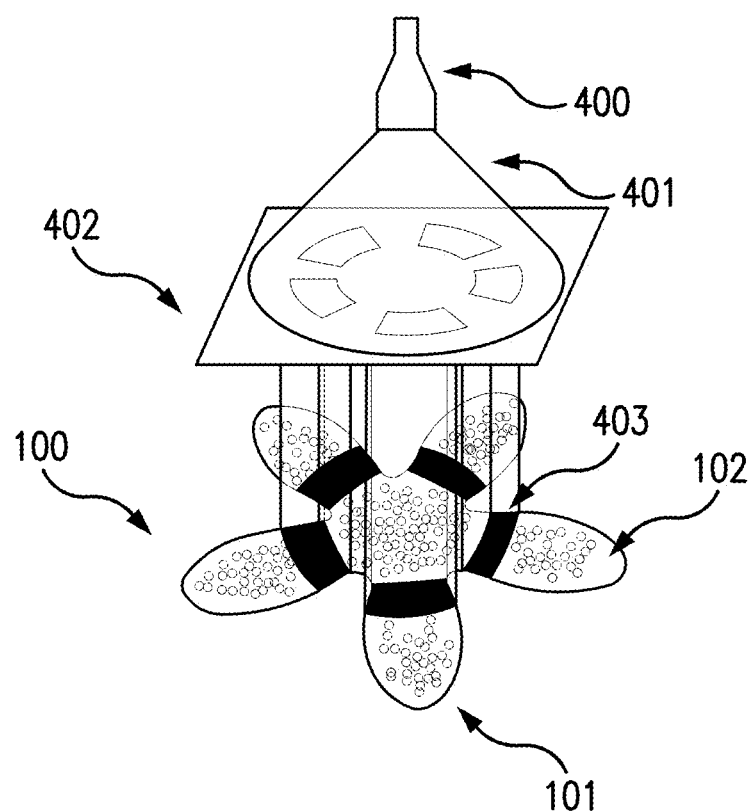
FIG. 4 is an illustration of a method for fabricating a water based actuator in accordance with some embodiments of the disclosed subject matter.

Referring to FIG. 4, an illustration of an example method for fabricating a water-based actuator 100 is shown. UV light 401 can be applied to the deposited solution 102 by a light source 400, and through a lithography mask 402. UV light 401 can be transmitted only through defined areas of a lithography mask 402 pattern, curing or coupling only some of the deposited solution 102 to the first layer 101, making pattern features 403.

In some embodiments, the light source 400 can be Splice Lamp (Norland P/N 5200) which can provide 2,500 $\mu W/cm^{-2}$ intensity in the proximity mode. In some embodiments, the lithography mask 402 can be kept out of contact with the deposited solution 102 by using a spacer (not shown). In some embodiments, the lithography mask can be intentionally contacted to the substrate. The lithographic mask 402 can include Chromium, film, or acrylic sheets, among others. In some embodiments, with an acrylic sheet, a pattern feature 403 size can range from about 10 μm to about 10 mm and with Chromium masks, the pattern feature 403 size can range from about 1 μm to about 100 μm.

Figure 5:
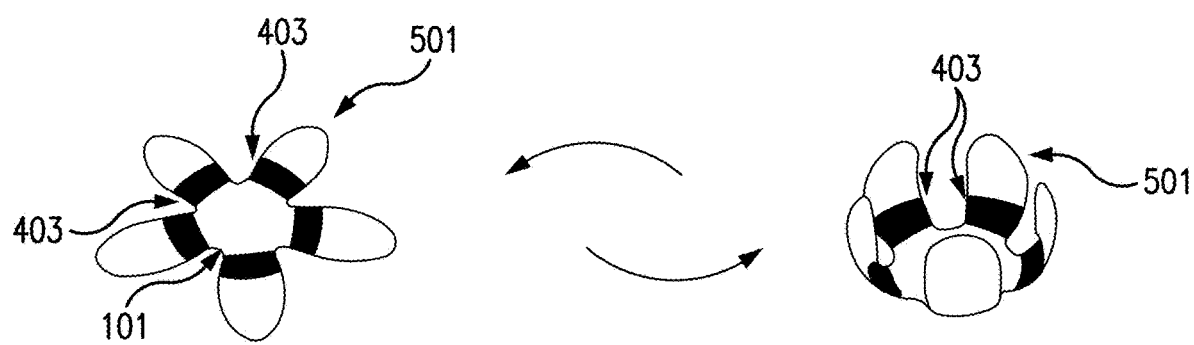
FIG. 5 is an illustration of a water responsive actuator in accordance with some embodiments of the disclosed subject matter.

Referring to FIG. 5, an example actuator is shown. The pattern features 403 can bend the first layer 101 in specific parts, separating the first layer 101 into moving parts 501 and non-moving parts. Accordingly, the actuator can be a flat surface when exposed to humid air and fold into a 3D structure when exposed to dry air, as seen in FIG. 5. An electrical heater (not shown) can be used to affect local humidity. Electrical heaters can include resistive heating elements that are part of the actuator.

Figure 6:
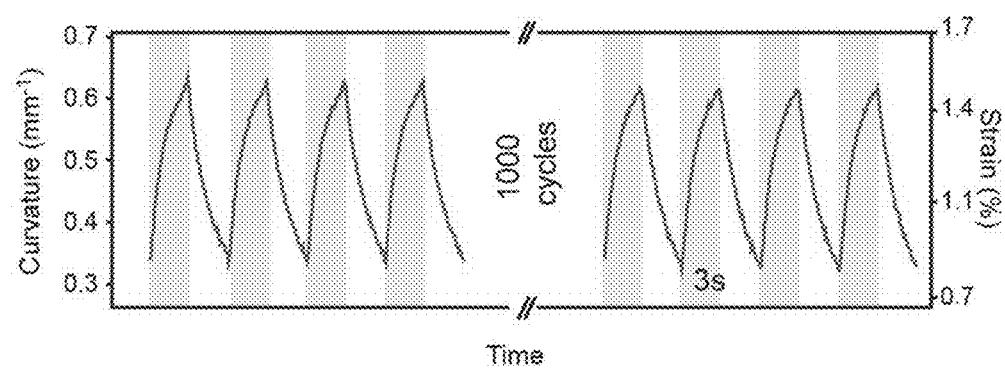
FIG. 6 is a graph of the time trace of an example actuator before and after 1000 actuation cycles in accordance with some embodiments of the disclosed subject matter.

FIG. 6 is a graph of the time trace of an example actuator before and after 1000 cycles. Such actuators can experience a negligible change in performance after repeated use.

Figure 7A:
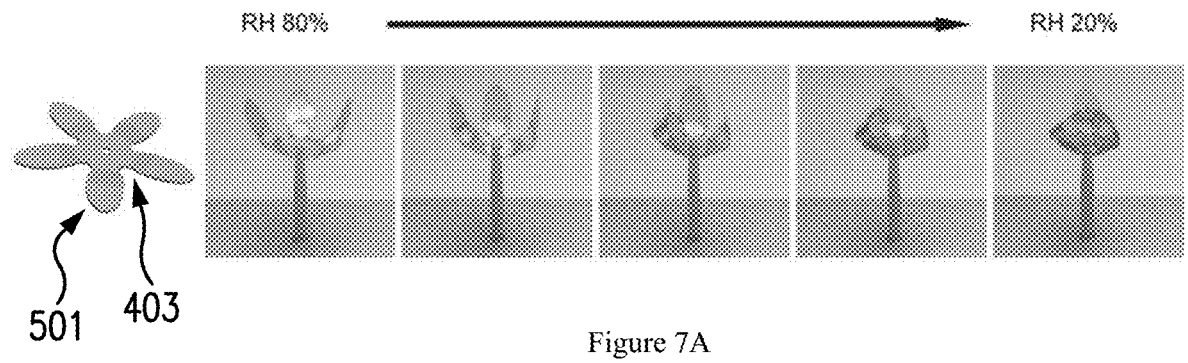
FIG. 7 illustrates three example actuators in accordance with some embodiments of the disclosed subject matter.
Figure 7B:
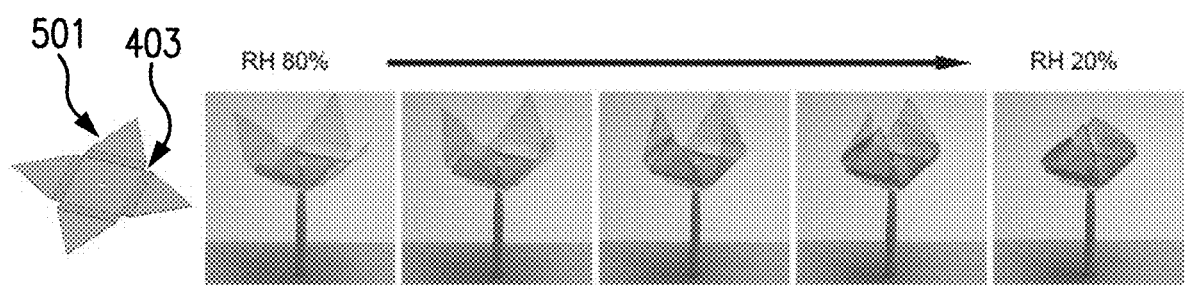
Figure 7C:
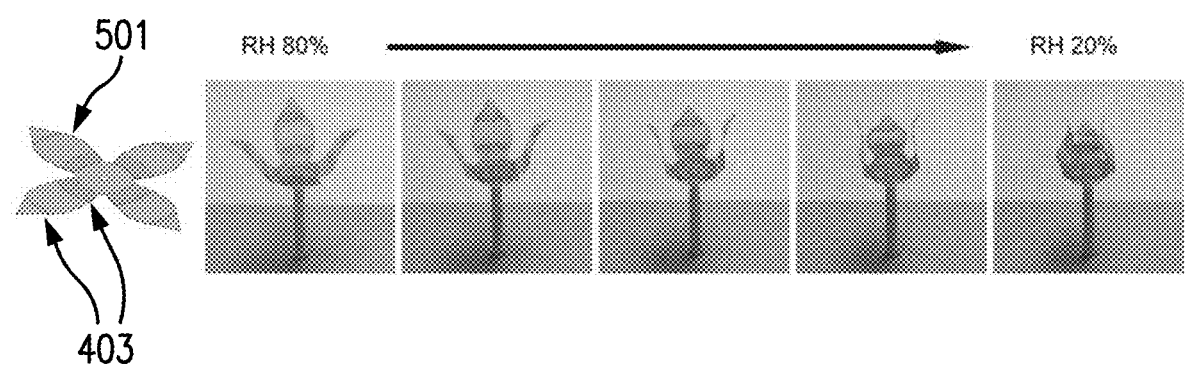

Referring to FIG. 7, three example water responsive actuators are shown. In the illustrated example embodiments, pattern features 403 include joints, which can contract when exposed to dry air and can thereby bend the first layer 100. FIG. 7a shows an example actuator with a flower shape. FIG. 7b shows an example actuator in a pyramid shape. FIG. 7c shows an example actuator in a tulip shape. The pattern features 403 can expand when exposed to humid air and can thereby return the first layer 101 to its original position.

In some embodiments, the disclosed method can be performed on multiple sides of the first layer 101, resulting in an actuator that can move in more complicated ways, for example having part of the first layer 101 bend in one direction and another part bend in the other, as seen in FIG. 7c. Example actuators with different designs can be made, for example, a flower (FIG. 7a) pyramid (FIG. 7a) and tulip shapes (FIG. 7a). The joints 403 can be patterned with photolithography and enable folding and unfolding of the moving pieces 501 upon changes in the relative humidity.

The tulip shape (FIG. 7c) can be fabricated with a two-mask process. The first mask can be for patterning the joints on the topside of the first layer 101, which enables the larger motion. The second mask can be used for patterning the joints on the backside of the first layer 101, for creating the out-of-axis curvature at the edges of the moving pieces. It can take approximately 20 seconds for an example relative humidity testing chamber to vary between 20% to 80%. Unfolding and folding speed for the samples can match this time scale. The actuators can return to their initial state after every cycle.

Figure 8:
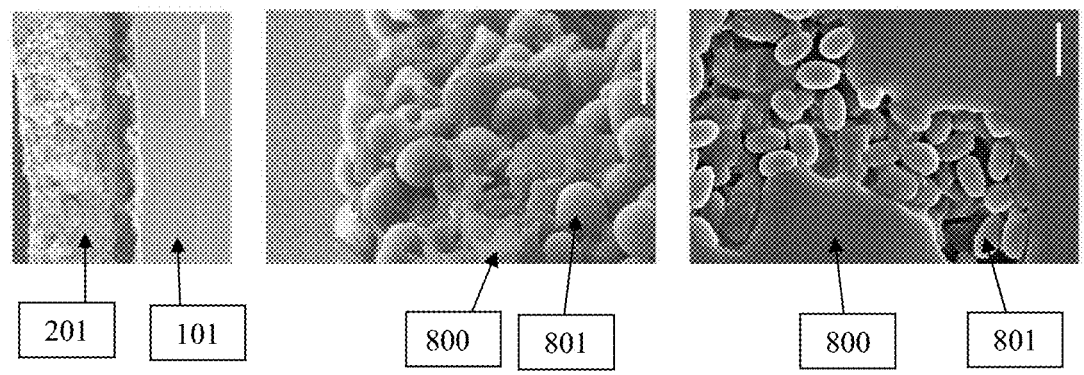
FIG. 8 is SEM cross sectional image of an example actuator in accordance with some embodiments of the disclosed subject matter.

FIG. 8 contains SEM images of an example actuator, which shows the two layers in an example actuator 101 and 201, as well as the bacterial spores 801 suspended in the adhesive 800. The bacterial spores 801 can include, for example, *Bacillus subtilis* spores, cotE-gerE mutant of *Bacillus subtilis*, or *Bacillus thuringiensis* spores. The UV cured adhesive 800 can be water insoluble.

Figure 9:
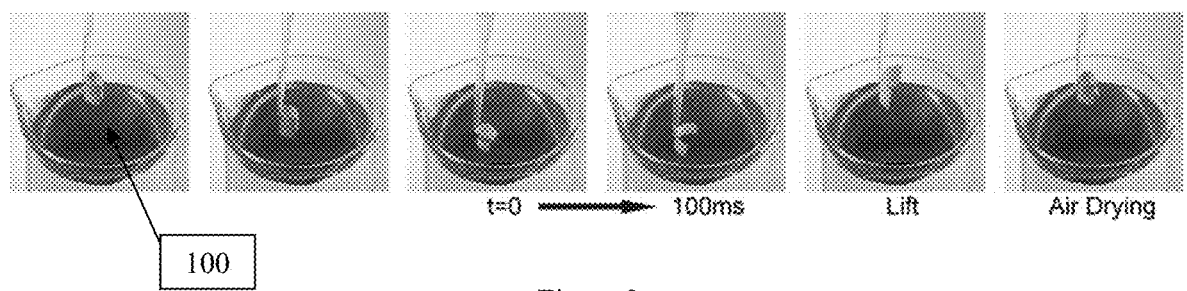
FIG. 9 is a series of images that illustrate an example actuator being triggered by liquid water contact.

Referring to FIG. 9, an example bent actuator 100 "pops up" in 100 ms after it is completely submerged into water. Afterwards, it is lifted and dried with blowing dry air. It goes back to its original condition after drying. Even after several submerging cycles, the example actuator can return to its original condition.

When an example actuator is dipped inside liquid water, the second layer 201 is saturated with water molecules which can result in a fast response time. The moisture transport need not be solely via airflow, and poroeleastic swelling in the spores can become the dominant factor defining the limits of actuation speed. After drying, the example actuator can go back to its original shape, and can be ready for consecutive actuation cycles. This feature can occur as follows. First, bacterial spores, which are the source of humidity responsive behavior, are dormant and they do not lose their capabilities in aqueous media. Second, the adhesive is not water soluble and does not lose its adhesiveness inside the water. Hence the example actuator can keep its integrity and the active layer does not delaminate from the polyimide substrate.

Figure 10:
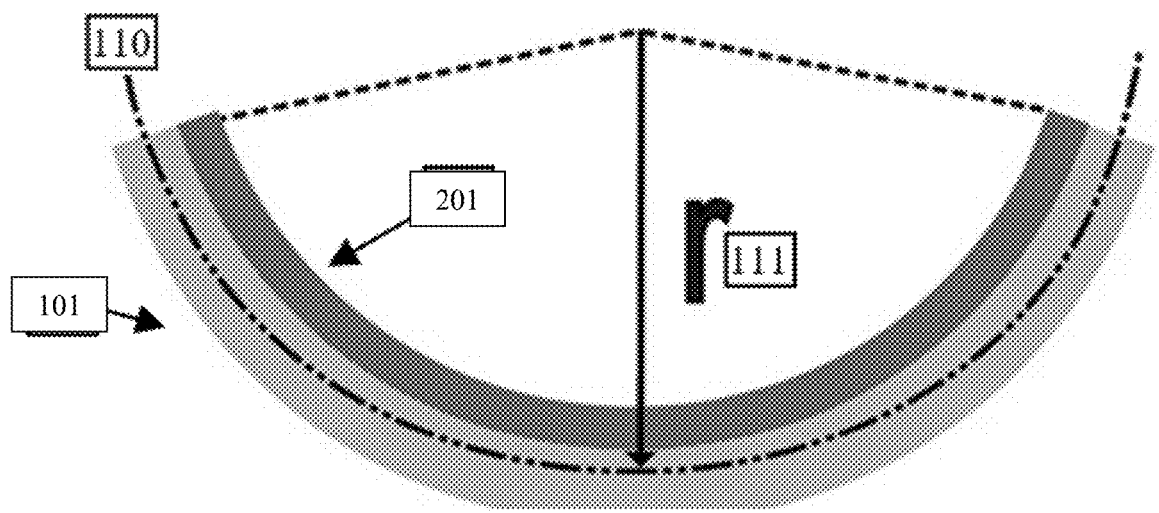
FIG. 10 is an illustration of a side view of an example actuator in accordance with some embodiments of the disclosed subject matter.

FIG. 10 is an illustration of a side view of an example actuator in a curved state.

Figure 11:
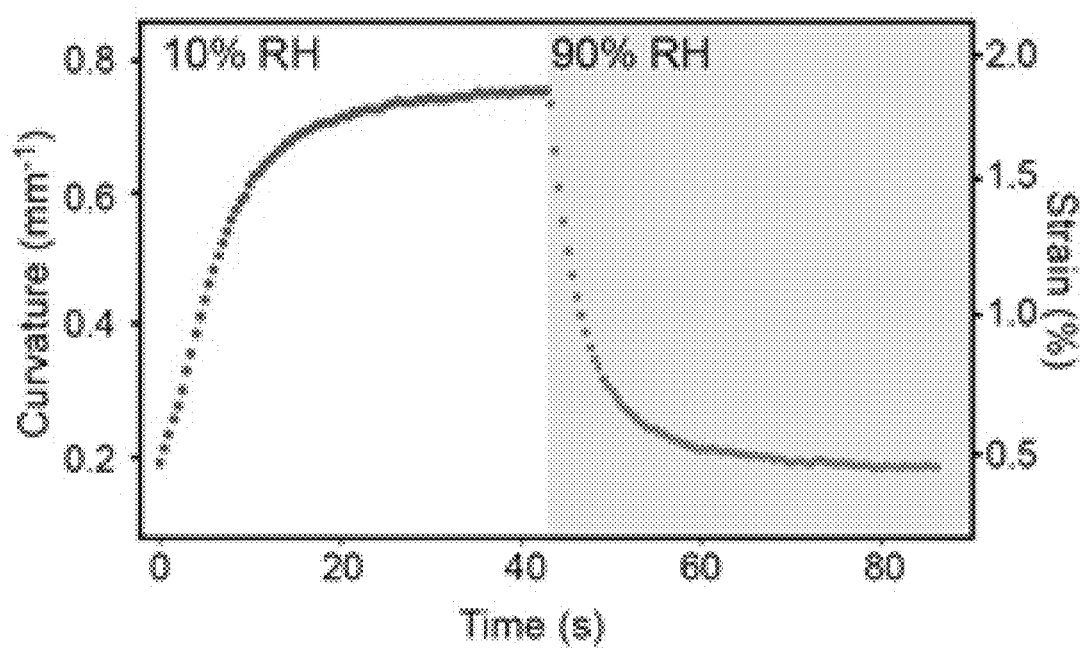
FIG. 11 is a graph of the change in the curvature (1/r) and strain of an example actuator in accordance with some embodiments of the disclosed subject matter.

FIG. 11 is a graph of the change in the curvature (1/r) and strain of a sample actuator during consecutive dehydration and hydration cycles of an example actuator. The example measurements were made during consecutive dehydration and hydration cycles. Radii of curvature (r) can be determined by using known techniques, for example, a suitable circle fitting script. An exponential curve is fit to the data points to obtain time constant ($\tau$).

In certain embodiments, the response time of the actuator can be controlled by tuning the adhesive-to-solution volume ratio. For example, by increasing the amount of adhesive 800 relative to spore 801, or by increasing the thickness of the deposited solution 102, the response time can be increased. For example, the adhesive can be provided in a ratio of about 0.1% to about 5% by volume to the solution The response time can be adjusted to be between about 100 milliseconds and about 3 minutes. In general, increasing the amount of adhesive, either by increasing the volume ratio of the adhesive to other constituents in the solution or by increasing the thickness of the deposited solution, tends to slow down response time of the actuator, but also increases the energy density required to cause activation. In certain embodiments, individual pattern features 403 can be tuned for a specific response time by tuning their adhesive-to-solution volume ratio ratios. An exemplary method can include using a mixture of spores 801 and UV-curable optical adhesives 800 suspended in a solvent. Example solvents include acetone or toluene. Example spores includes *Bacillus subtilis* and mutants thereof, or other spores that change volume when exposed to water or humidity.

The wavelength of the UV light 401 that cures the solution 102 can be varied, for example, based on the adhesive specifications. The adhesives can be cured with low power UV-light 401, which can simplify the process or with high power UV-light which can enable faster curing and speed up fabrication of actuators. For example, light with any wavelength between about 200 nanometers and about 700 nanometers can be used.

In certain embodiments, the performance, durability, and fabrication complexity of the actuators can be adjusted by adjusting the properties of the adhesive 800. For example, a stiff and ductile adhesive 800 can increase force transmission. In certain embodiments, adhesives 800 with Young's Modulus in 0.5-2 GPa range and durability under high elongation, e.g., an elongation of 35%, can be used. The mixing ratios are obtained by dividing the volume of the adhesive to the total volume of the spore/adhesive layer. An adhesive that is not water soluble can be used and can improve the ability of an example actuator to remain functional after liquid water contact. In some embodiments, the actuator can remain functional after being exposed to water multiple times, and maintain substantially the same functionality and reversibility after such exposure. The actuator can retain functionality even after extended use, e.g., 1000 humidity response cycles. An example actuator that has improved functionality retention can be used in a range of applications.

Samples taken out of a UV chamber can exhibit curvature when acetone is substantially evaporated. Sample actuators can vary the amount they fold as the relative humidity changes. For example, at 90% relative humidity, example actuators can be almost completely unfolded, and at 20% relative humidity, example actuators can be completely folded to the point of being cylindrical, as seen in FIG. 3. Although a broad change in relative humidity can permit complete folding and unfolding, actuators made in accordance with the disclosed subject matter can exhibit actuation, e.g., in the form of partial folding and unfolding, when operating between even a narrow humidity range, e.g., between 30% and 20%, as shown for example in FIG. 7. The fast curing of the adhesive and high evaporation rate of the acetone can both contribute to swift fabrication.

In some embodiments, the curing time can be less than a minute. The curing time can depend on the thickness of the deposited solution layer 102, but even for a layer more than 20 micrometers thick, 1 min of total curing time can be sufficient. In some embodiments, solution that remains uncured can be removed, for example by dipping into an alcohol based solvent or wiping with a swap.

In an example experimental embodiment, an energy density (0.83 MJ/m$^3$) was obtained using 50% adhesive content. A power density (91 kW/m$^3$), on the other hand, was achieved with 40% adhesive content samples. The effect of the adhesive-to-spore mixing ratio can be salient. Samples with higher adhesive content can have higher energy densities regardless of the adhesive type. This can be because the voids between the spores are filled with the adhesive more densely, which results in better energy transmission between spores and the substrate.

The power densities, however, do not necessarily show the same trend. Increasing adhesive concentration can lead to increasing the strain energy, but also in slower actuation. The adhesive filled voids can impede the penetration of water molecules through the layer, which can explain why power densities with 40% adhesive content tend to be larger than the ones with 50%, even though the latter ones generally exhibit higher energy densities. The effect of thickness on actuator dynamics can also be similar. In most of the samples, when the spore layer thickness is increased, the total strain energy increases. However, it can take more time for water molecules to transport inside a thicker layer, which results in slower actuation and lower power densities.

In some embodiments, the location of the neutral axis is determined by:

$$H = t_2 - \frac{E_1^2 t_1^4 + E_1 E_2 t_1 t_2^2 (3t_1 + 4t_2)}{6E_1 E_2 t_1 t_2 (t_1 + t_2)} \qquad (1)$$

Where H defines the location of the neutral axis at the cross section 110, $t_1$ is thickness of the adhesive layer 201, $t_2$ is the thickness of the first layer 100. $E_1$ and $E_2$ is the Young's Modulus of the adhesive layer 201 and first layer 101 respectively. The area moment of inertia (I) is modified using the parallel axis theorem:

$$I = \frac{bh^3}{12} + bh\left(\frac{t_2}{2} - H\right)^2 \qquad (2)$$

In some embodiments, the bending strain energy of the actuators, U can be calculated by:

$$U = \frac{EI}{r^2} L \qquad (3)$$

In (3), E is the Young's Modulus of the first layer 101, r is the radius of curvature 111, L is the length of the sample and I is the area moment of inertia with respect to the neutral axis. From the measured radius of curvature 111, r, the total energy transferred to the polyimide substrate can be determined. Energy density can be defined as the energy produced by unit volume of spore. Hence, it can be calculated by dividing the strain energy of each actuator by the spore volume on it. Power density can be obtained by dividing energy density value to the time constant (τ). The change in the curvature with respect to time can be plotted and an exponential fit can be applied to the data. The time constants (τ) of different samples can be obtained from exponential fits. The radius of curvature and time constant can be used to determine the strain energy and power of the actuators.

Energy densities up to, e.g., 1 MJ/m3 can be achieved with the disclosed subject matter. The disclosed subject matter can facilitate development of biologically-based actuators for applications including energy harvesting, construction of complicated 3D folding structures, and soft robotic applications, among others.

An example actuator was tested in an environmental room where the RH and temperature was maintained at 20% and 25° C. respectively. An example actuator with a rectangular geometry (6 mm×12 mm) was prepared. In the dry state the example actuator curves and exhibits a cylindrical geometry. The sample was attached to pipette tip which was connected to a motorized linear actuator (Derock Heavy Duty Linear Actuator, Amazon) to enable smooth soaking of the sample without any splash. The example actuator was soaked inside the distilled water and lifted back to the initial position. The liquid water on the actuator was wiped with a piece of laboratory wiper (Kimtech Science Kimwipes, Delicate Task Wipers) and the example actuator dried with blowing dry air (~5%).

The flower, pyramid and tulip shaped actuators and photolithography masks can be designed using Adobe Illustrator CS6 software. The geometries can be cut from a 30 cm×30 cm polyimide film (Kapton Tape 0.5 mil (12.5 micrometers), Colepalmer) using a laser cutter (Epilog Mini 24, CO2 laser system), creating a first layer 101. The lithography masks can be machined from a 3 mm thick black acrylic piece (McMaster) using the same laser cutter system. An acrylic mask can be chosen because they can be easy to machine and low-cost materials. Acrylic masks can provide satisfactory resolution and small feature size to fabricate centimeter scale actuators. Standard photolithography tools such as film or chromium masks can also be utilized for smaller feature size requirements.

The prepared first layers 101 with the unfolded flower, pyramid or tulip shapes can be placed on a Polydimethylsiloxane (PDMS) coated acrylic holder. The PDMS can provide a sticky surface due to its electrostatic interaction with polyimide tape and can enable fixing of the sample for the alignment process. The first layer 101 surface can be cleaned with ethanol and the spore/adhesive suspension 102 can be pipetted on the first layer 101 uniformly, similar to maskless fabrication. The photolithography mask 402 can be aligned to the substrate using guidance holes which can be machined both on the holder and on the mask. The UV light 401 can be applied with a Splice Lamp (Norland P/N 5200) which provides 2,500 micro W/cm2 intensity in the proximity mode. A proximity gap of 50 micrometers can be achieved with a spacer. After 1 minute of UV exposure the first layer 101 can be peeled smoothly from the holder with a tweezer and it can be dipped inside the IPA for 20 seconds to remove the uncured parts. Next, the uncured solution 102 can be cleaned with a wet swap do get rid of any residue. A second mask process can be conducted for the tulip, where the same procedure can be applied to the backside of the first layer 101.

A chamber can be built to vary humidity around example actuators quickly and measure the responses of the actuators. It can be made of acrylic parts which can be machined with a laser cutter (Epilog Mini 24, CO2 laser system). The volume of the chamber can be kept small to enable fast humidity change. A stream of air can be passed through the chamber. The RH of the air can be controlled by mixing dry air (5%) provided by laboratory air source and humid air (~95 RH) generated by passing laboratory air through a bubbler (e.g., an airstone from JW Pet Company can be used to bubble air into water in an Erlenmeyer flask) in a controlled fashion. A second source with lower flow rate can be mixed with the main stream to set the minimum value to ~10% and maximum value to ~90% and prevent RH exceed that limit values. A solenoid valve (SMC NVFS1120-6G-01T valve sol/pilot 12vdc) controlled by a custom LabVIEW interface can be used to switch between the humid and dry states. A humidity sensor (Digikey, 480-3538-ND, Sensor Humidity 5v Anlg 3.5% Sip) can be placed next to the sample to monitor the humidity inside the chamber. The sensor also can be connected to the same LabVIEW interface. The sample can be attached to a vertical rod inside the chamber with a small piece of double-sided tape. The response of the actuators to the humidity change can be recorded with a digital camera.

Functionality retention after contact with liquid water can be desirable for various reasons. A humidity responsive actuator that retains functionality after contact with liquid water can be used for adaptive textiles and clothes. The human skin can be a source of humidity but since the sweat is in liquid phase it can damage the actuator if it is not water resistant. This can also enable washing of adaptive textiles. Humidity responsive actuators that retain functionality after contact with liquid water can also provide a power source for wearable electronics and sensor applications. Since they can be compatible with the sweat in both liquid and gas phases they can be used to generate work and power for other wearable devices. For example, this feature can be used to make sensors to measure a sweat rate of human users. This can enable continuous monitoring of the sweat rate of users (e.g., athletes), which can be useful in various contexts.

Water responsive actuators that retain functionality after contact with liquid water can also provide marine robotics applications. They can also be used for different outdoor conditions, including rain and snow, for adaptive architecture designs, and in the interface of different liquids such as oils, solvents or water. They can generate force and displacement when the media surrounding them is altered. This can enable the use of this kind of actuator in enclosed liquids and such embodiments.

Water responsive actuators that retain functionality after contact with liquid water can also be used to create stroke for naval vehicles in various scales. They can be stacked and generate stroke when dipped inside the water. For the small scale, they can be used for toy applications. They can be used for soft robotics applications that require gripping and handling; objects to transfer from air to liquid media or from liquid to air media. A soft robotics gripper which can work in both environments without losing function is desirable and can be achieved using humidity responsive actuator that retains functionality after contact with liquid water.

The description herein merely illustrates the principles of the disclosed subject matter. Various modifications and alterations to the described embodiments will be apparent to those skilled in the art in view of the teachings herein. It will thus be appreciated that those skilled in the art will be able to devise numerous techniques which, although not explicitly described herein, embody the principles of the disclosed subject matter and are thus within its spirit and scope.

The invention claimed is:

1. A water-responsive actuator comprising:

a substantially planar first layer comprising a flexible material that substantially maintains its shape in the presence of water; and a second layer positioned on a surface of the first layer;

wherein the second layer comprises a cured solution including a bacterial spore and a cured adhesive, the second layer being water-responsive to permit repeatable actuation in the presence of water, wherein the cured solution comprises the cured adhesive in a ratio of 0.1% to 5% by volume to the solution.

2. The actuator of claim 1, wherein the bacterial spore comprises a *Bacillus subtilis* spore.

3. The actuator of claim 1, wherein the second layer comprises a patterned layer.

4. The actuator of claim 1, wherein the water responsive actuator further comprises an electrical heater adapted to affect local humidity.

5. The actuator of claim 1, wherein the second layer is adapted to be electrically conductive.

6. The actuator of claim 1, wherein the cured adhesive comprises an adhesive having a Young's Modulus of between 1 GPa to 2 GPa.

7. The actuator of claim 1, wherein the second layer is adapted for actuation by contact with liquid water.

8. The actuator of claim 1, wherein the second layer is adapted for actuation by contact with liquid water and to return to an initial shape by cessation of such contact with liquid water.

9. The actuator of claim 1, wherein the second layer is adapted for actuation by contact with air having a relative humidity of at least 30%.

10. The actuator of claim 1, wherein the second layer is adapted for actuation by contact with air having a first relative humidity and to return to an initial shape by contact with air having a second relative humidity, wherein said second relative humidity is at least 10% less than said first relative humidity.

* * * * *